(12) United States Patent
Glasl et al.

(10) Patent No.: US 8,222,439 B2
(45) Date of Patent: Jul. 17, 2012

(54) PROCESS FOR THE PRODUCTION OF CARBOXYLIC ACID ESTERS

(75) Inventors: Wolfgang Glasl, Graz (AT); Martin Mittelbach, Graz (AT); Matthaeus Siebenhofer, Graz (AT); Erich Jeitler, Hartberg (AT); Wilhelm Hammer, Grambach/Graz (AT); Helmut Gossler, Graz (AT); Michael Koncar, Lieboch (AT)

(73) Assignee: BDI Biodiesel International AG, Graz (AT)

( * ) Notice: Subject to any disclaimer, the term of this patent is extended or adjusted under 35 U.S.C. 154(b) by 489 days.

(21) Appl. No.: 11/996,734

(22) PCT Filed: Jul. 24, 2006

(86) PCT No.: PCT/AT2006/000311
§ 371 (c)(1),
(2), (4) Date: Mar. 26, 2008

(87) PCT Pub. No.: WO2007/012097
PCT Pub. Date: Feb. 1, 2007

(65) Prior Publication Data
US 2008/0227994 A1    Sep. 18, 2008

(30) Foreign Application Priority Data
Jul. 25, 2005   (AT) ................ A 1245/2005

(51) Int. Cl.
C11C 3/00    (2006.01)
C11B 3/00    (2006.01)

(52) U.S. Cl. ......... 554/169; 554/174; 554/167; 554/170

(58) Field of Classification Search .......... 554/192, 554/195
See application file for complete search history.

(56) References Cited

U.S. PATENT DOCUMENTS

| 4,319,017 A * | 3/1982 | Kosanovich et al. ......... 528/176 |
| 5,525,126 A * | 6/1996 | Basu et al. ...................... 44/308 |
| 6,124,486 A | 9/2000 | Cherwin et al. |
| 2008/0033192 A1* | 2/2008 | Siano et al. ................... 554/174 |

FOREIGN PATENT DOCUMENTS

| CH | 481045 | 11/1969 |
| DE | 2824782 | 12/1978 |
| DE | 19942541 | 3/2001 |
| IT | MI20041323 A1 * | 9/2004 |
| WO | WO 2006006033 A1 * | 1/2006 |

OTHER PUBLICATIONS

ITMI20041323 (A1), ASER SRL, Sep. 30, 2004, (abstract) (1 page).*
Database CA [Online] Chemical Abstracts Service, Columbus, Ohio, US; Domide, Teodor et al: "Manufacture of epoxy resin esters of fatty acids or rosin" XP002408436 retrived from STN Database accession No. 112:99953 abstract & RO 95 945 B1 (Centrul De Cercetari Pentru ProtectII Anticorsive Lacuri Si Vopsele,) Sep. 15, 1988.

* cited by examiner

*Primary Examiner* — Yate K Cutliff
(74) *Attorney, Agent, or Firm* — Birch, Stewart, Kolasch & Birch, LLP

(57) ABSTRACT

The invention relates to a process for the production of carboxylic acid esters by esterification of carboxylic acids and/or transesterification of carboxylic acid esters with alcohols in the presence of a liquid metal catalyst, characterized in that the liquid metal catalyst is the alkaline earth metal salt of a carboxylic acid.

11 Claims, No Drawings

PROCESS FOR THE PRODUCTION OF CARBOXYLIC ACID ESTERS

This application is the National Phase Under 35 U.S.C. §371 of PCT International Application No. PCT/AT2006/000311 which has an International filing date of Jul. 24, 2006, which designates the United States of America, and claims priority to Austrian Application No. A 1245/2005 which has a filing date of Jul. 25, 2005, the entire contents of all applications listed above are hereby incorporated by reference.

The invention relates to a process for the production of carboxylic acid esters by esterification of carboxylic acids or transesterification of carboxylic acid esters with alcohols in the presence of a liquid metal catalyst.

By transesterification, the alcoholysis of triglycerides is meant, that is, the reaction with lower alcohols, in particular methanol and ethanol, whereby the monoesters of fatty acids as well as glycerol are formed via the intermediates di- und monoglycerides.

By the term "triglycerides", esters of higher, saturated and/or unsaturated fatty acids with glycerol are understood. Such esters are, for example, main constituents of oils and fats of a vegetable or animal origin. Many fats of a natural origin but also used waste fats and used edible oils contain free fatty acids in more or less high amounts. These fats are thus a mixture of triglycerides, free fatty acids and other components, wherein the triglycerides normally constitute the main constituent of said mixture.

Fatty acid esters, in particular the methyl esters, are important intermediates in oleochemistry. In Europe alone, 200,000 tons of vegetable oil methyl ester are produced annually as raw materials especially for surfactants. In addition, fatty acid methyl ester is gaining ever more importance as a fuel for auto-ignition engines.

Basic catalysts (alkali hydroxides, alcoholates, oxides, carbonates, anion exchangers), acid catalysts (mineral acids, p-toluenesulfonic acid, boron trifluoride, cation exchangers) and enzymes (lipases) can be used as catalysts for transesterification. Today, catalysts which are soluble in the reaction mixture are preferably used. These catalysts form a homogeneous mixture and ensure fast conversion rates and mild reaction conditions. The homogeneous catalysts used most commonly are sodium and potassium hydroxide as well as sodium methylate, which are admixed to the vegetable oil after having been dissolved in alcohol. Such a process is known from AT-B 386 222. The acidic catalysis requires higher reaction temperatures and pressures and a more complex reaction control. An acidic transesterification is known from FR-A-85 02340.

The transesterification involving a basic catalysis is generally performed without using a solvent. The reaction starts with a two-phase system of triglyceride and alcohol, however, with the reaction progressing and ester being formed, a homogeneous phase is formed which, in turn, becomes diphasic due to the formation and precipitation of glycerol, wherein the light phase is the raw fatty acid alkyl ester and the heavy phase is a phase rich in glycerol.

From EP-A 1 477 551, heterogeneous catalyst systems are known which are composed of salts of transition metals, among other things of manganese. Furthermore, a catalyst system of sodium/potassium hydroxide and sodium/potassium soaps is described.

In DE-A 19949718, a transesterification in the presence of transition metal soaps is described. EP-A 1 308 498 also describes esterification and transesterification reactions in the presence of alkali soaps. Zinc soaps are also mentioned as possible catalysts.

From U.S. Pat. No. 6,818,026, a process is known in which the operation is run under supercritical conditions in the presence of solid catalysts. Among other things, magnesium oxide is also mentioned as a catalyst. In terms of transesterification rates with magnesium oxide, only 91% is indicated, however.

In U.S. Pat. No. 6,147,196, a transesterification process in three stages is described, with two stages concerning a heterogeneously catalyzed transesterification and one stage concerning a distillation of esters and the separation of a bottom product as well as the recirculation of the bottom product to the first stage. As catalysts, zinc aluminate is used, the catalyst does not reach the distillation and is not returned along with the bottom product.

U.S. Pat. No. 6,187,939 in turn describes a catalyst-free process in the supercritical range.

DE-A 19942541 describes esterifications and transesterifications of carboxylic acids and carboxylic acid esters in the presence of heavy metal compounds as catalysts.

The processes of the prior art particularly have the disadvantage that the reaction proceeds with losses because, among other things, free fatty acids are still present in the reaction mixture. This is where the present invention sets in, which aims at eliminating said disadvantage.

The process according to the invention for the production of carboxylic acid esters by esterification of carboxylic acids or transesterification of carboxylic acid esters with alcohols in the presence of a liquid metal catalyst is characterized in that the liquid metal catalyst is the alkaline earth metal salt of a carboxylic acid.

The alkaline earth metal is preferably magnesium, and the carboxylic acid is preferably an aliphatic carboxylic acid, especially with 10 to 24 carbon atoms in the molecule.

An aliphatic monohydric alcohol, in particular methanol or ethanol, is preferably used as the alcohol.

In particular triglycerides, which preferably are fats and oils of a vegetable or animal origin, especially used edible oils and waste fats, are used as the carboxylic acid esters to be esterified or transesterified, respectively.

In the process according to the invention, carboxylic acids and carboxylic acid esters, e.g. fats and/or oils of a vegetable and/or animal origin, are esterified and/or transesterified with alcohols, for example from the group of monohydric C1 to C4 alcohols, into carboxylic acid alkyl esters.

The catalysts can be formed by reacting inorganic metal compounds, e.g. metal oxides and/or metal hydroxides, with carboxylic acids, e.g. fatty acids, prior to the esterification or transesterification reaction, respectively.

Preferably, the reaction occurs at an increased temperature, especially at temperatures above 150° C., preferably above 200° C. The pressure during the reaction corresponds to the vapour pressure of the mixture at the given temperature and can optionally be set even higher than said vapour pressure, e.g. higher by up to 20 bar.

In the process according to the invention, turnovers of more than 90% are achieved in the esterification and transesterification. After the reaction stage, the reaction mixture is separated, whereby the following products are obtained: unreacted alcohols, carboxylic acids and carboxylic acid esters as well as water from the charge stocks, alcohols formed by the reaction, carboxylic acid esters and water, and the catalyst.

The process stages are exemplified by way of the production of fatty acid esters from oils and/or fats, which can also contain free fatty acids and water, by esterification or transesterification, respectively, with an alcohol, for example from the group of $C_1$ to $C_4$ alcohols.

During the reaction, the fats and oils are converted into fatty acid esters and glycerol by transesterification with the alcohol that is used. The free fatty acids react with the alcohol that is used and form fatty acid esters and water. After the reaction, the excess alcohol and the water present in the reaction mixture are first separated from the reaction mixture. This separation is preferably done by evaporation of the alcohol and the water. However, the separation could also be effected with the aid of membrane methods or adsorptive and extractive methods.

After the separation of water and alcohol, unreacted mono-, di- or triglycerides, the catalyst (e.g. the metal soaps) and low-volatile impurities are separated from the mixture. Since the mixture thus separated contains the catalyst, in the following, it is referred to as a catalyst mixture. This separation can be accomplished by membrane methods, crystallization methods, adsorption methods or extraction methods. A separation of the catalyst alone is feasible also by means of ion exchangers. Preferably, however, the separation is brought about by distillation. In a distillation apparatus, the fatty acid ester phase and the glycerol phase are thereby separated as an overhead product from the catalyst mixture accumulating as a bottom product, preferably under negative pressure (0.1-10 mbar absolute).

Prior to the separation of the catalyst mixture from the glycerol or fatty acid ester phase, respectively, the mixture from the reaction stage can optionally be mixed with metal compounds (e.g. oxides or hydroxides), which subsequently form the metal soaps. In doing so, free fatty acids present in the reaction mixture are saponified, whereby the separation of the catalyst mixture from the ester and glycerol phase is facilitated. This addition of metal compounds can also occur prior to or after the separation of alcohol and/or water. This route also opens up the possibility to introduce a catalyst into the process.

A separation between the fatty acid ester phase and the glycerol phase can optionally occur prior to the separation of the catalyst mixture, and the separation of the catalyst mixture from the fatty acid ester phase and the glycerol phase can be carried out separately. In this case, the same methods as mentioned above, preferably a distillation, can be applied.

Thereupon, the fatty acid ester phase from the separation step of the catalyst mixture can be supplied to purification processes. A wash with polar liquids as well as ion-exchange methods, absorption methods, extraction methods or further distillation steps are suitable purification methods.

The purified fatty acid ester phase can be used, for example, as a fuel. The glycerol phase obtained after the separation of the catalyst mixture can be supplied to further purification steps. These purification steps can comprise ion-exchange processes, absorptive processes, extractive processes and distillation processes. After distillation and after a subsequent treatment with activated carbon, pharmaceutical glycerol, for example, can be obtained.

The obtained catalyst mixture can be returned to a new reaction stage (esterification or transesterification, respectively) without further processing and is able to act there again as a catalyst for the esterification and transesterification reaction. However, the catalyst can also be separated from the catalyst mixture and returned in the pure form. The separation of the catalyst can be effected using precipitation, crystallization, membrane, ion-exchange, adsorption, extraction or distillation methods. One specific possibility is the precipitation of the alkali metal/alkaline earth metal compounds with water. By oxidizing the catalyst mixture, the organic components of said mixture can be destroyed and the metals can be returned as inorganic compounds to or in front of the reaction stage. Via carboxylic acids, these metal compounds are reconverted into the required catalyst compounds.

The obtained catalyst mixture can be returned either completely or partially. A partial discharge of the catalyst mixture has the advantage that, in this manner, impurities are also discharged from the process.

Recirculation can be effected either directly into the reaction chamber or into the charge stocks before they are fed into the reaction chamber.

The first reaction stage for esterification and transesterification can be followed by further reaction stages, wherein the byproducts formed (mainly water and alcohols formed) can preferably be separated after each reaction stage and fresh catalyst as well as fresh alcohol is optionally added to the reaction mixture in each reaction stage. The reaction can be run discontinuously or continuously, wherein, seen from an energetic point of view, the continuous process control involving a recovery of heat is to be preferred.

The process according to the invention provides major advantages especially for the production of fatty acid esters from vegetable and/or animal fats and/or oils by esterification and/or transesterification with alcohols, e.g. from the group of C1 to C4 alcohols. In comparison to the process described in DE-A 19942541, the process according to the invention has noticeably better conversion rates. The comparative examples also show that the esterification proceeds very well especially with magnesium soaps and that hardly any free fatty acids are present in the reaction mixture. This provides advantages for the separation of the reaction mixture, since, e.g. during distillation, free fatty acids are discharged with the fatty acid esters partially into the overhead product, whereby the quality of the fatty acid esters is downgraded.

Most established processes for the production of fatty acid esters from fats and oils via transesterification with alcohol work with basic catalysts. These processes can only work with largely anhydrous and fatty acid-free raw materials. In these processes, the catalyst is destroyed, fresh catalyst has to be added again and again, the costs associated therewith are correspondingly high. For KOH, for example, catalyst costs amounting to approx. 7 to 9 EUR per ton of fatty acid ester have to be expected. With the process according to the invention, the catalyst is recovered, however, which is why, with the present process, the catalyst costs remain below 1 EUR per ton of fatty acid ester.

The present process has the advantage that free fatty acids at arbitrary concentrations can also be provided in the initial mixture. These free fatty acids are likewise esterified into fatty acid alkyl esters during the above-mentioned reaction. Thus, low-quality fats/oils are processible as well. Another decisive advantage of the process is that the esterification/transesterification reaction can also be carried out in the presence of water. It thereby becomes possible to use also aqueous raw materials, especially aqueous alcohols.

Unreacted free fatty acids or glycerides are likewise returned to esterification/transesterification, thereby avoiding losses.

Compared to catalyst-free processes, the process according to the invention provides the advantage that the reaction proceeds with smaller hyperstoichiometric amounts of alcohol, which, in turn, clearly improves the efficiency of the process, since the expenditure for the recovery of the alcohol is smaller than with processes without a catalyst.

By way of the following example, preferred variants of the process according to the invention are described in even greater detail.

EXAMPLE 1

In a series of comparisons, different catalysts for the esterification and transesterification, respectively, of carboxylic acid esters were tested. The following chemicals were used:
rape oil from 00 rape seed, deslimed, deacidified, deodorized, dried,
oleic acid, technically pure,
methanol, technically pure,
water, deionized,
as catalysts in a technically pure grade:
tetrabutyl titanate,
dibutyltin dilaurate,
magnesium stearate,
calcium stearate,
sodium stearate With all the above-mentioned catalysts, the following experiments were carried out: In each case, 150 g of rape oil, 37.5 g of oleic acid and 123 g of methanol were mixed with the amount of catalyst as indicated in Table 1 and were made to react in a laboratory autoclave at 210° C. for a period of 30 minutes. After the reaction, it was possible to measure the indicated concentrations of fatty acid methyl ethyl ester (FS methyl ester) in the ester phase.

TABLE 1

| catalyst | catalyst [mol cat/kg oil] | amount of metal [g met/kg oil] | triglycerides [% by weight] | diglycerides [% by weight] | monoglyceride [% by weight] | free fatty acids [% by weight] | FS methyl esters [% by weight] |
|---|---|---|---|---|---|---|---|
| tetrabutyl titanate | 0.066 | 3.2 | 5.5 | 9.7 | 11.3 | 4.8 | 69.0 |
| magnesium stearate | 0.134 | 3.3 | 0.3 | 1.8 | 4.3 | 0.1 | 92.2 |
| dibutyltin dilaurate | 0.027 | 3.2 | 1.1 | 8.8 | 11.8 | 4.2 | 72.7 |
| calcium stearate | 0.080 | 3.2 | 0.4 | 2.3 | 6.4 | 4.0 | 86.8 |
| sodium stearate | 0.138 | 3.2 | 9.9 | 14.2 | 13.1 | 6.2 | 56.6 |
| tetrabutyl titanate | 0.134 | 6.4 | 1.7 | 5.7 | 9.7 | 3.8 | 79.1 |
| dibutyltin dilaurate | 0.134 | 5.9 | 0.4 | 6.1 | 8.4 | 3.8 | 80.0 |

It is evident that, with the amount of metal being the same, far better turnovers can be achieved in the mixture with alkaline earth compounds. This applies both to weight ratios and to molar ratios.

The entire reaction product was filled into a laboratory distiller. In said distiller, methanol and water were removed by distillation from the reaction mixture, at first under normal pressure. Then, the bulk of the methyl ester phase and of the glycerol phase was separated by distillation under a pressure of about 0.5 mbar. The organometallic compounds acting as a catalyst remained in the bottom residue during this distillation. Said residue was again mixed with rape oil and oleic acid as well as with methanol and was again delivered to an esterification/transesterification reaction. The selected mass ratios can be seen in Table 2.

TABLE 2

| | oil, fatty acids, catalyst mixture [g] | methanol [g] | composition of the ester phase after the reaction | | | | |
|---|---|---|---|---|---|---|---|
| catalyst | | | triglycerides [% by weight] | diglycerides [% by weight] | monoglycerides [% by weight] | free fatty acids [% by weight] | fatty acid esters [% by weight] |
| tetrabutyl titanate | 190.79 | 124.0 | 1.6 | 5.9 | 9.5 | 4.7 | 78.2 |
| magnesium stearate | 187.55 | 121.9 | 0.1 | 2.5 | 5.0 | 0.1 | 92.4 |
| dibutyltin dilaurate | 93.3 | 125.7 | 2.5 | 6.5 | 9.8 | 4.8 | 76.4 |
| calcium stearate | 87.74 | 122.1 | 0.1 | 2.3 | 6.4 | 4.0 | 86.8 |
| sodium stearate | 82.76 | 118.8 | 1.8 | 7.2 | 14.2 | 4.0 | 72.8 |

The conditions for the second reaction stage were again chosen such that the product was kept at a temperature of 210° C. for a period of 30 minutes. The content of methyl ester in the methyl ester phase after said second reaction stage is likewise illustrated in Table 2. The higher turnover with alkaline earth metal catalysts is clearly recognizable.

Also after the second reaction, the mixture was separated by distillation (separation of methanol and water), which was followed by the distillation of methyl ester and glycerol. The ester phases from both distillations were in each case separated from the glycerol phases (by gravity sedimentation) and were subsequently washed with 0.5% by weight of water. The ester thus obtained met the quality requirements of EN 14214. The yield which could be achieved with the individual catalysts is summarized in Table 3. It can clearly be seen that a far better yield was achieved with alkaline earth catalysts than with heavy metal catalysts.

TABLE 3

| Yield of fatty acid methyl ester, based on the applied amount of oleic acid and fatty acid | |
|---|---|
| tetrabutyl titanate | 74% |
| magnesium stearate | 94% |
| dibutyltin dilaurate | 77% |

TABLE 3-continued

| Yield of fatty acid methyl ester, based on the applied amount of oleic acid and fatty acid | |
|---|---|
| calcium stearate | 88% |
| sodium stearate | 68% |

EXAMPLE 2

In 2 test series in a continuously operating pilot plant, the following raw materials were processed within a period of 5 days each: used edible oil with a content of free fatty acids of approx. 7% (used edible oil: used edible oils from households and businesses contain a mixture of different vegetable and animal fats and oils, free fatty acids, water, other impurities, e.g. from deep-frying processes), and animal fat from an animal cadaver processing plant with a content of free fatty acids of approx. 14%.

Magnesium oleate was used as the catalyst. To prepare the catalyst, 4 kg of magnesium oxide and 44 kg of oleic acid were reacted with each other at about 60° C. for a period of 2 hours and were then held available for the processing of oils and fats, respectively.

Processing comprised the following steps: At first, the mixture of oil/fat was mixed with methanol and the catalyst. Using a pump, this mixture was pumped from the mixing container into a storage vessel. Using another pump, the mixture was pumped continuously with a flow rate of 25 l/h from said storage vessel into the plant. At first, the mixture was conducted through a heat exchanger and heated to 215° C. After the heat exchanger, the mixture continued to flow through a reactor, the residence time in the reactor amounted to 30 minutes, the pressure was set to 50 bar abs by means of a throttle valve arranged after the reactor.

The desired esterification reactions (free fatty acids and methanol into fatty acid methyl ester and water) and transesterification reactions (glycerides and methanol into fatty acid methyl ester and glycerol) proceeded in the heat exchanger and in the reaction vessel. Via the throttle valve, the reaction mixture was expanded to atmospheric pressure, whereby methanol and water evaporated and were separated in the subsequent flash container. The remaining mixture was conducted to a further degassing stage, which was run at 140° C. and 50 mbar abs, whereby residual amounts of water and methanol were separated.

After this degassing procedure, the remaining mixture was separated continuously in a short-path distilling apparatus into a bottom product mainly containing unreacted glycerides, fatty acids, the catalyst and small amounts of methyl ester, and into an overhead product accumulating in the form of two liquid phases, a methyl ester phase and a glycerol phase. These phases were conducted through a gravity separator and were thus separated from each other. The glycerol phase comprised about 99.5% of glycerol. The methyl ester phase was washed with 0.5% by weight of water in a mixing container, the water phase was separated in a gravity separator, and subsequently the ester phase was dried at 120° C. and approx. 100 mbar abs in a flash container. Thereafter, the methyl ester was provided in a quality which met the EN 14214 standard. Only the required CFPP value could not be achieved for animal fat ester and used edible fat for the winter. The bottom product was collected in a container and subsequently was mixed again with further raw material in the mixing container and thus was used again for the catalysis of the above-mentioned reactions.

Within a period of 5 days, this process was run continuously for each raw material for 24 hours each. The amounts summarized in the following Table 4 were processed and obtained, respectively:

The used edible oil had a polymer content of 5.5%. Since, in case of used edible oil, the yield of fatty acid methyl ester amounts to almost 97%, these polymers were also converted largely into methyl ester. In the bottom product, the polymer concentration was below 1%.

COMPARATIVE EXAMPLE

The raw material amounts of used edible oil and animal fat as indicated in Example 2 were mixed with potassium methanolate and methanol according to the prior art in order to perform a transesterification into the respective methyl ester. For this purpose, potassium hydroxide (technical, approx. 88%) was first of all dissolved in methanol (technically pure). The amounts were chosen such that a solution with a KOH concentration of 8% was obtained. Said solution was mixed with the above-mentioned fats at a ratio oil:solution=10:1.5. After a reaction time of 20 minutes at about 40° C. and a subsequent settling time of 12 hours, no phase separation occurred, the catalyst potassium methylate had become inactive due to saponification reactions with the fatty acids present in the raw materials. After addition of concentrated sulfuric acid until a pH-value of 4 was reached in the reaction mixture, the respective reaction mixture was separated into an oil/fat phase and a methanol/glycerol phase. The yield of methyl ester in the oil/fat phase amounted to only about 15%.

The invention claimed is:

1. A process for the production of carboxylic acid esters by esterification of carboxylic acids and/or transesterification of carboxylic acid esters with methanol or ethanol in the presence of a liquid metal catalyst,
    characterized in that
    the liquid metal catalyst is the alkaline earth metal salt of a carboxylic acid and that, upon completion of the esterification or transesterification, respectively, the metal catalyst is used for another esterification or transesterification, respectively and wherein said carboxylic acid is an aliphatic carboxylic acid comprising 10 to 24 carbon atoms.

2. A process according to claim 1, wherein the alkaline earth metal is magnesium.

3. A process according to claim 1, wherein the carboxylic acid esters to be esterified or transesterified are triglycerides.

4. A process according to claim 3, wherein fats and oils of a vegetable or animal origin are used as triglycerides.

5. A process according to claim 4, wherein said fats and oils are edible oils or waste fats.

6. The method according to claim 1, wherein said esterification and/or transesterification in the presence of a liquid metal catalyst is conducted at a reaction temperature of above 200° C.

7. A process for the production of carboxylic acid esters comprising:
    a) reacting a carboxylic acid and/or a carboxylic acid ester with methanol or ethanol in the presence of a liquid metal catalyst at a temperature of above 200° C.,

TABLE 4

| | charge oil/fat | methanol | catalyst | water | products methyl ester | glycerol | waste water | methanol | bottom | methyl ester yield |
|---|---|---|---|---|---|---|---|---|---|---|
| used edible oil | 846.0 | 691.7 | 10.2 | 7.6 | 820.0 | 80.0 | 8.3 | 600.4 | 47.0 | 96.9% |
| animal fat | 842.0 | 615.4 | 10.4 | 7.2 | 827.0 | 81.5 | 7.9 | 534.3 | 31.0 | 98.2% | whereby said carboxylic acid is esterified and/or said carboxylic acid ester is transesterified, and b) repeating step (a) with said liquid metal catalyst; wherein the liquid metal catalyst is an alkaline earth metal salt of a carboxylic acid and said carboxylic acid is an aliphatic carboxylic acid comprising 10 to 24 carbon atoms.

8. The process according to claim 7, wherein the alkaline earth metal is magnesium.

9. The process according to claim 7, wherein the carboxylic acid ester to be esterified or transesterified is a triglyceride.

10. The process according to claim 9, wherein said triglyceride is a fat or a oil of a vegetable or animal origin.

11. The process according to claim 10, wherein said fat or oil is an edible oil or waste fat.

\* \* \* \* \*